US00PP10822P

United States Patent [19]

Danziger

[11] Patent Number: Plant 10,822

[45] Date of Patent: Mar. 9, 1999

[54] PETUNIA PLANT NAMED 'DANPETSWEET'

[75] Inventor: Gabriel Danziger, Nir Zvi, Israel

[73] Assignee: Danziger-"Dan" Flower Farm, Moshav Mishmar Hashiva, Israel

[21] Appl. No.: 865,871

[22] Filed: May 30, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS 5,523,520 6/1996 Hunsperger et al. ..... 800/200

*Primary Examiner*—Howard J. Locker

*Attorney, Agent, or Firm*—Foley & Lardner

[57] ABSTRACT

A petunia plant named 'Danpetsweet' particularly characterized by its relatively small diameter, intense red-purple flower, open, loose slightly upright trailing growth habit, and good tolerance to various weather conditions.

2 Drawing Sheets

The present invention comprises a new and distinct cultivar of petunia, known by the cultivar name 'Danpetsweet'.

'Danpetsweet' was originated from a hybridization made by the inventor, Gabriel Danziger, in a controlled breeding program in Mishmar Hashiva, Israel in 1995. Both the male and female parents were proprietary unnamed petunia hybrids used in the breeding program.

'Danpetsweet' was discovered and selected as one flowering plant within the progeny of the stated cross by the inventor Gabriel Danziger in May 1995 in a controlled environment in Mishmar Hashiva.

The first act of asexual reproduction of 'Danpetsweet' was accomplished when vegetative cuttings were taken from the initial selection in June 1995 in a controlled environment in Mishmar Hashiva by a technician working under the supervision of the inventor. Horticultural examination of selected units was initiated in September 1995 and has demonstrated that the combination of characteristics as herein disclosed for 'Danpetsweet' are firmly fixed and are retained through successive generations of asexual reproduction.

'Danpetsweet', has not been observed under all possible environmental conditions. The phenotype may vary somewhat with variations in environment such as temperature, light intensity and day length, without any variations in genotype. The following observations, measurements and comparisons describe the plants grown in Mishmar Hashiva under greenhouse conditions which approximate those generally used in commercial practice.

The following traits have been repeatedly observed and are determined to be basic characteristics of 'Danpetsweet' which in combination distinguish this petunia as a new and distinct cultivar:

1. Relative small diameter flowers which rise above the foliage;
2. Open, loose, slightly upright trailing growth habit;
3. Intense red-purple flower color; and
4. Good weather tolerance. The plant grows vigorously under hot climate conditions and tolerates mild winter conditions in Israel. Plant recovers well after heavy rain.

Of the many commercial cultivars known to the inventor, there is no cultivar with which 'Danpetsweet' can be meaningfully compared.

In the accompanying photographic drawings, Sheet 1 is a top perspective view of 'Danpetsweet', showing typical flower and foliage characteristics of a plant grown in an open field under Israeli winter conditions. Therefore, the photographic drawing does not accurately reflect the open and loose growth habit of 'Danpetsweet' grown under greenhouse conditions which approximate those generally used in commercial practice.

Sheet 2 is a close-up view showing the corolla throat and flower vein details. The colors are as true as possible with illustration of this type In the following description color references are made to The Royal Horticultural Society Colour Chart. The color values were determined between 10:00–12:00 a.m. in October 1996 under full sunlight at Mishmar Hashiva, Israel.

Classification:

*Botanical.*—Petunia hybrid.

*Commercial.*—Petunia cultivar 'Danpetsweet'.

Plant:

*Growth habit.*—Open, loose, slightly upright trailing growth habit.

*Plant height.*—About 15 cm.

*Spreading area.*—About 89–102 cm.

*Blooming period.*—Throughout year.

*Chlorosis.*—Not exhibited.

Stem:

*Thickness.*—2–3 mm.

*Color.*—Green, R.H.S. 141D.

*Pubescence.*—Yes.

*Branching.*—Free.

*Length of internode.*—23–25 mm.

*Rooting.*—Stems do not root at the nodes when placed in moist soil. Cuttings under moist conditions do root.

Leaf:

*Arrangement on stem.*—Alternate.

*Shape.*—Oblong.

*Size.*—40 mm.

*Thickness.*—1.0 mm .

*Color.*—138A, upper surface.

*Pubescence.*—Yes.

Flower:

*Orientation at opening.*—Upright.

*Type.*—Single.

*Shape.*—The shape is regular with a rounded corolla that is united with 5 lobes and has a long straight tube.

*Diameter.*—37 mm, very small.

*Length of corolla.*—About 40 mm.

*Color.*—Upper surface: Main color is 74B; veins and throat on top surface is 90C. Lower surface: About 75A.

*Calyx.*—Narrow and linear in shape; 5 sepals, each about 12 mm in length, green in color and pubescent.

*Peduncle.*—Length: 35 mm. Color: Green.

*Reproductive organs.*—Pistil: Number: 1. Color: Green. Stamens: Number: 5. Anther: Gray-blue. Filament: Light purple.

Other characteristics: The cultivar does not set seeds. Pinching is required early in growth to induce a branched plant. Pinching generally delays the first flowering; however, after the initial pinching, flowering is fast and free with no additional pinching required.

Disease resistance: 'Danpetsweet' has not shown unusual susceptibility to common diseases of petunia and is resistant to most leaf diseases.

I claim:

1. A new and distinct cultivar of petunia plant named 'Danpetsweet' as herein shown and described.

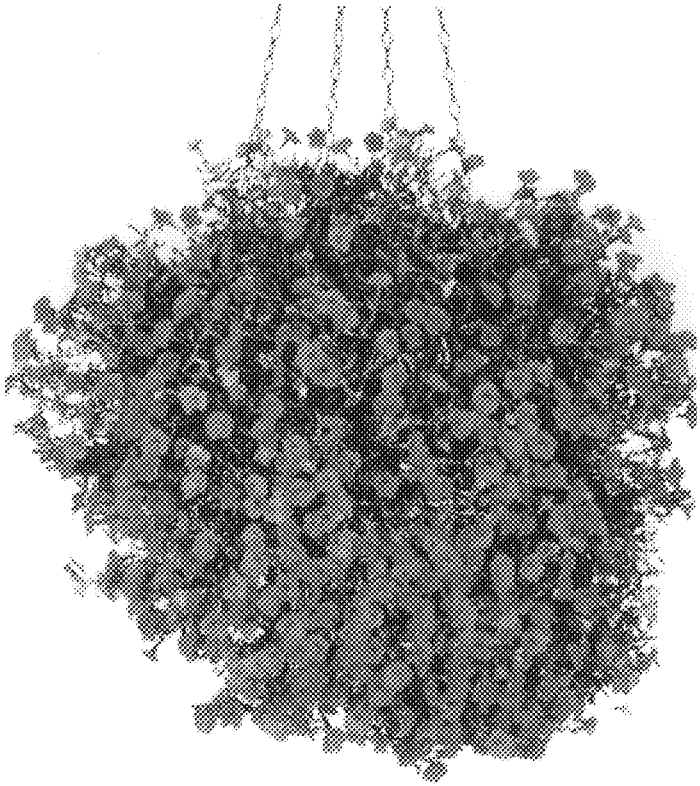

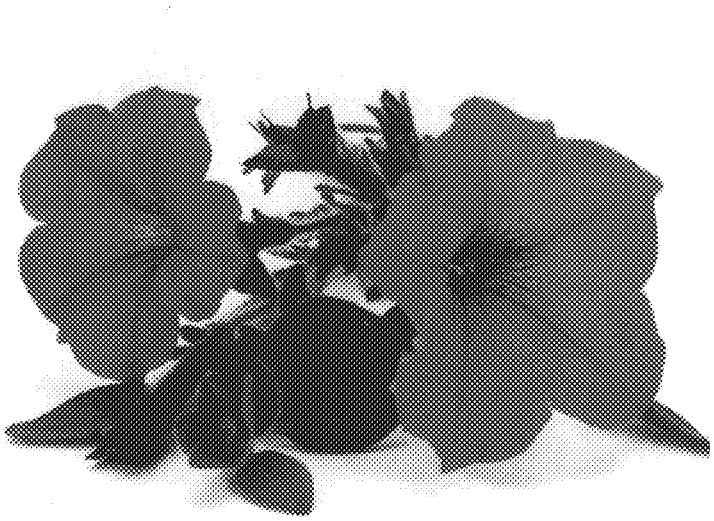

* * * * *